United States Patent [19]

Yarchoan et al.

[11] Patent Number: 5,665,345
[45] Date of Patent: Sep. 9, 1997

[54] METHODS OF INHIBITING VIRAL REPLICATION USING IL-10

[75] Inventors: Robert Yarchoan; M. Wayne Saville; Giovanna Tosato, all of Bethesda; Kazuyuki Taga, Rockville, all of Md.

[73] Assignee: The United States of America as represented by the Department of Health and Human Services, Washington, D.C.

[21] Appl. No.: 66,785

[22] Filed: May 24, 1993

[51] Int. Cl.$^6$ ........................................ A61K 45/05
[52] U.S. Cl. .................................. 424/85.2; 424/85.1
[58] Field of Search ........................ 424/85.1, 85.2, 424/85.7

[56] References Cited

PUBLICATIONS

Akridge et al., J. Immunol., vol. 153, pp. 5782–5789, 1994.

Kootstra et al., J. Virology, vol. 68(11), pp. 6967–6975, 1994.

Emilie et al., Int. J. Immunopharmac., vol. 16 (5/6) pp. 391–396, 1994.

Fiorentino, D. F., M. W. Bond, and T. R. Mosmann. 1989. Two types of mouse T helper cell. IV. Th2 clones secrete a factor that inhibits cytokine production by Th1 clones. *J. Exp Med.* 170:2081.

Howard, M., A. O'Garra, H. Ishida, R. De Waal Malefyt, and J. De Vries. 1992. Biological properties of interleukin–10. *J Clin Immunol.* 12:239.

Go, N. F., B. E. Castle, R. Barrett, R. Kastelein, W. Dang, T. R. Mosmann, K. W. Moore, and M. Howard. 1990. Interleukin 10, a novel B cell stimulatory factor: unresponsiveness of X chromosome–linked immunodeficiency B cells. *J Exp Med.* 172:1625.

Bogdan, C., Y. Vodovotz, and C. Nathan. 1991. Macrophage deactivation by interleukin 10. *J Exp Med.* 174:1549.

de Waal Malefyt, R., J. Abrams, B. Bennett, C. G. Figdor, and J. E. de Vries. 1991. Interleukin 10(IL–10) inhibits cytokine synthesis by human monocytes: an autoregulatory role of IL–10 produced by monocytes. *J Exp Med.* 174:1209.

Vieira, P., R. de Waal Malefyt, M. N. Dang, K. E. Johnson, R. Kastelein, D. F. Fiorentino, J. E. deVries, M. G. Roncarolo, T. R. Mosmann, and K. W. Moore. 1991. Isolation and expression of human cytokine synthesis inhibitory factor cDNA clones: homology to Epstein–Barr virus open reading frame BCRFI. *Proc Natl Acad Sci U S A.* 88:1172.

Thorley–Lawson, D. A. 1980. The suppression of Epstein–Barr virus infection in vitro occurs after infection but before transformation of the cell. *J Immunol.* 124:745.

Masucci, M. G., M. T. Bejarano, G. Masucci, and E. Klein. 1983. Large granular lymphocytes inhibit the in vitro growth of autologous Epstein–Barr virus–infected B cells. *Cell Immunol.* 76:311.

Gazzinelli, R. T., M. Makino, S. K. Chattopadhyay, C. M. Snapper, A. Sher, A. W. Hugin, and H. C. Morse III. 1992. CD4+ subset regulation in viral infection. Preferential activation of Th2 cells during progression of retrovirus–induced immunodeficiency in mice. *J Immunol.* 148:182.

Benjamin, D., T. J. Knobloch, and M. A. Dayton. 1992. Human B–cell interleukin–10: B–cell lines derived from patients with acquired immunodeficiency syndrome and Burkitt's lymphoma constitutively secrete large quantities of interleukin–10. *Blood.* 80:1289.

Mosier, Donald E., Richard J. Gulizia, Paul D. MacIsaac, Bruce E. Robett and Jay A. Levy. 1993. Rapid Loss of CD4$^+$ T Cells in Human–PBL–SCID Mice by Noncytopathic HIV Isolates. Science, vol. 260, pp. 689–692.

Poli, G., A.L. Kinter, D. Weissman, P. Biswas and A.S. Fauci. 1993. Interactions Between Pro–Inflammatory and Immunoregulatory Cytokines Modulate the Expression of Human Immunodeficiency Virus in Monocytic Cells. Clinical Research, vol. 41, No. 2.

Chan et al., J. Exp Med, vol. 173, pp. 869–879, 1991.

Brok et al., J. Immunol., vol. 151, No. 11, pp. 6451–6459, 1993.

Roitt et al., "Immunology", Third Edition, Publishers: Mosby, Baltimore, pp. 8.12 to 8.16, 1993.

Saville et al., Blood, vol. 83(12), pp. 3591–3599, Jun. 1994.

Montaner et al., The Lancet, vol. 344, pp. 625–626, 1994.

Butera, J. Cell. Biochem., vol. 53, pp. 336–342, 1993.

Martin et al., Cancer Res., vol. 46, pp. 2189–2192, 1986.

Fox, BioTech., vol. 12, p. 128, 1994.

Fahey et al., Clin. Exp. Immunol., vol. 88, pp. 1–5, 1992.

Lane et al, The New England J Med, vol. 311(17), pp. 1099–1103, 1984.

Lane et al., Annals of Int. Med., vol. 103, pp. 714–718, 1985.

Hirsch, The Amer. J. Med., vol. 85 (Suppl. 2A), pp. 182–185, 1988.

Konrad, "Biological Barriers to Protein Delivery", ed. Audus et al., Plenum Press, pp. 409–437, 1993.

(List continued on next page.)

*Primary Examiner*—Chhaya D. Sayala
*Attorney, Agent, or Firm*—Needle & Rosenberg

[57] ABSTRACT

The present invention provides a method of inhibiting the replication of human immunodeficiency virus in cells which are infected with HIV comprising administering to the cells a replication inhibiting amount of interleukin-10. Also provided is a parenteral method of the administration of interleukin-10 administration. Further provided is a method of inhibiting retroviral replication in a human subject infected by a retrovirus, comprising administering to the subject an inhibiting amount of interleukin-10, including the retrovirus is. Finally, a method of treating Kaposi's sarcoma in a human subject comprising administering to the subject an effective amount of interleukin-10 to the subject is provided.

30 Claims, No Drawings

PUBLICATIONS

Meijer et al., Antiviral Res., vol. 18, pp. 215–258, 1992.
Wedner, Basic & Clin. Immunol., Ed Stites et al., Appleton & Lange, Chap 34, 1991.
Jansen et al., Pharm. Res., vol. 10(11), pp. 1611–1614, 1993.
Hsu et al., Int. Immunol., vol. 4 (5) pp. 563–569, 1991.
Folks et al., PNAS, vol. 86, pp. 2365–2368, 1989.
Osborn et al., PNAS, vol. 86, pp. 2336–2340, 1989.
de Waal Malefyt, J Exp Med., vol. 174, pp. 1209–1220, 1991.
Perno et al Blood, vol. 80, No. 4 (Aug. 15) 1992 pp. 995–1003.
Perno et al The Journal of Experimental Medicine, vol. 169, (Mar. 1989) pp. 993–951.
Clerici, Mario et al., "Changes in Inteleukin-2 and Interleukin-4 Production in Asymptomatic, Human Immunodeficiency Virus–seropositive Individuals", The Journal of Clinical Investigation, Inc., vol. 91, pp. 759–765, Mar. 1993.

METHODS OF INHIBITING VIRAL REPLICATION USING IL-10

BACKGROUND OF THE INVENTION

1. Field of the Invention

This invention relates to the immune system. Specifically, the invention provides the use of a cytokine, interleukin-10 (IL-10), to inhibit viral replication.

2. Background Art

The cytokine IL-10 (previously called cytokine synthesis inhibitory factor) was initially identified in 1989 as a factor secreted by murine Th2 cell clones that inhibits the secretion of interferon gamma (IFN-γ) and other cytokines by Th1 cells (1). In addition, IL-10 appears to mediate some of the B cell stimulatory effects of Th2 cells, and this cytokine thus appears to be involved in shifting the balance of an immune response away from cellular and towards humoral immunity (2, 3). Additional studies have shown IL-10 to have immunomodulatory effects by acting on macrophages and other cell types. In particular, IL-10 suppresses the secretion of various cytokines by activated macrophages (4, 5), costimulates mast cell growth (6), and costimulates thymocyte growth in the presence of IL-2 and/or IL-4 (7).

Soon after the discovery of murine IL-10, the human IL-10 gene was identified and cloned (8). Human IL-10, which has activities similar to that of murine IL-10, has been found to be produced by cells of several lineages including B lymphocytes (9, 10) and monocyte/macrophages (M/M) (5, 11). Human and murine IL-10 were found to exhibit extensive sequence homology to BCRF-1, a previously uncharacterized open reading frame in the genome of Epstein Barr virus (EBV) (8). Moreover, this viral protein was found to retain a number of IL-10 activities (12). It has been speculated that BCRF1 may be a "trapped" cellular genes that may confer a selective advantage to EBV, perhaps by directly contributing to the stimulation of EBV-infected B cells, or by helping the EBV-infected cells evade immune surveillance (13, 14).

It has also been suggested that a dysregulation between Th1 and Th2 cells, perhaps in part mediated by IL-10, might contribute to the pathogenssis of acquired immunodeficiency (AIDS). In a murine experimental model for AIDS induced by LP-BM5 murine leukemia virus, IL-10 overexpression has been found to correlate with a shift towards Th2 helper cells, B cell hyperactivation, down-regulation of Th1 cytokine secretion, and impaired CD8+ T cell function (15). Recent data from patients infected with human immunodeficiency virus (HIV) suggest that disease progression is associated with increased secretion of Th2 cytokines and downregulation of Th1 cytokines (16).

In the case of parasitic infections, it has been noted that IL-10 inhibits the production of reactive nitrogen oxides, which are involved in the elimination of intracellular *Toxoplasma gondii* (30) and the extracellular killing of *Schistosoma mansoni* by macrophages (30–32). It has been speculated that induction of IL-10 production may be a means by which parasites escape cell-mediated immunity (33).

In a murine retroviral model of AIDS, there is evidence to suggest that overexpression of IL-10 may contribute to disease pathogenesis by simultaneously suppressing cellular immunity and stimulating B cell hyperactivity (15).

These data suggest that IL-10 overexpression may be advantageous to vital replication and may actually contribute to disease progression. Contrary to these data, the present invention provides that IL-10 can actually be used to inhibit viral replication, especially the replication of HIV in human monocytes, macrophages or monocyte derived cells. Thus, the invention provides an urgently needed means to prevent HIV replication and treat diseases caused by HIV.

SUMMARY OF THE INVENTION

The present invention provides a method of inhibiting the replication of human immunodeficiency virus in cells which are infected with HIV comprising administering to the cells a replication inhibiting amount of interleukin-10.

Also provided is a method of treating a disease caused by human immunodeficiency virus in a human subject comprising administering a replication inhibiting amount of interleukin-10 to the subject.

Further provided is a method of inhibiting retroviral replication in a human subject infected by a retrovirus, comprising administering to the subject an inhibiting amount of interleukin-10, including the retrovirus is.

Finally, a method of treating Kaposi's sarcoma in a human subject comprising administering to the subject an effective amount of interleukin-10 to the subject is provided.

DETAILED DESCRIPTION OF THE INVENTION

The invention provides a method of inhibiting the replication of human immunodeficiency virus (HIV) in human monocytes, macrophages or monocyte derived cells comprising administering to the cells a replication inhibiting amount of interleukin-10. The examples set forth data showing the inhibition of monocytes/macrophages (M/M). In addition, HIV replication in monocyte derived cells such as microglial can likewise be inhibited.

The invention also provides a method of treating a disease caused by human immunodeficiency virus in a human subject comprising administering a replication inhibiting amount of interleukin-10 to the subject. The disease, for example, can be acquired immunodeficiency syndrome, human immunodeficiency virus disease, human immunodeficiency virus associated dementia and autoimmune disease caused by HIV infection.

The invention further provides a method of inhibiting retroviral, e.g. HIV, replication in a human subject infected by a retrovirus comprising administering to the subject an inhibiting amount of interleukin-10.

The invention still further provides a method of treating Kaposi's sarcoma in a human subject comprising administering to the subject an effective amount of interleukin-10 to the subject. Kaposi's sarcoma is a tumor involving the skin and internal organs that frequently develops in patients infectioned with human immunodeficiency virus. Kaposi's sarcoma is a frequent cause of morbidity and mortality in patients infected with human immunodeficiency virus. While the pathogenesis of Kaposi's sarcoma is not completely understood, it is believed that abnormal cytokine production associated with HIV replication in various cells (including monocyte-derived cells) is important in the development of this syndrome. Thus, interfering with HIV replication in monocyte/macrophages (for example by interleukin 10) is expected to result in amelioration of Kaposi's sarcoma.

As used herein, "interleukin-10" (IL-10) can mean the intact protein or substitutions, addition, or deletions which do not substantially diminish the replication inhibiting activity of IL-10. Thus, the BCRF1 gene product can be included in this definition. The Examples set forth the use of both human and mouse IL-10, with recombinant human IL-10 (rhIL-10) being by far most inhibitory.

Fragments of IL-10 can be generated, for example, by mechanical or chemical disruption of the complete protein. Modifications to IL-10 can be obtained by cloning modified nucleic acids encoding the polypeptide in an expression system capable of producing the modified protein or fragments thereof (see generally Sambrook et al. (55)). Modified nucleic acids encoding IL-10 can be made, for example, by site directed mutagenesis, by making synthetic genes having the modification, or by making nucleic acid fusions. A fusion can be used, for example, to increase the solubility of the protein. The activity of such a modified IL-10 or fragments can be determined utilizing the methods taught below in the Examples.

The aforementioned methods involve administration of IL-10 to a human subject. The compounds can be administered by means well known to those of skill in the art for administration of proteins. Such means, and the proper dosages, are exemplified by the administration of such proteins as insulin, interleukin-2 and immunoglobulins, for example, as are known to those of skill in the art. Parenteral and sublingual administration are typically preferred. In addition, the IL-10 can be administered to blood cells removed from the body of the subject and returned after treatment.

The exact amount of such IL-10 required will vary from subject to subject, depending on the species, age, weight and general condition of the subject, the severity of the disease that is being treated, the particular IL-10 used, its mode of administration, the side effects encountered, and the like. Generally, when administered to cells the amount of IL-10 administered is between about 0.001 and 1 units/ml, especially between about 0.01 and 0.1 units/ml. When administered directly to the subject, the amount of IL-10 administered is between about 1,000 and 1,000,000 units, especially between about 20,000 and 200,000 units. The appropriate amount can be maximized using standard procedures.

The IL-10 will preferably be in unit dosage form suitable for single administration of a precise dosage and may include an effective amount of the selected compound in combination with a pharmaceutically acceptable carrier, for example, saline. The units used here are defined as the amount that will produce half maximal stimulation of the MC9 mast cell line (6). By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. Actual methods of preparing such dosage forms are known, or will be apparent, to those skilled in this art; for example, see Remington's Pharmaceutical Sciences (561).

Parenteral administration is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

The data shows that HIV replication in monocytes is inhibited by rhIL-10 at concentrations that cause little or no cellular toxicity and that do not suppress cytokine secretion in response to LPS. This inhibition was observed with a 2-day exposure to IL-10, starting at the time of viral inoculation as well as 5 and 14 days after viral infection. rhIL-10 also caused partial suppression of viral production in certain monocytoid or T cell lines, albeit at higher concentrations. This invention teaches that one activity of IL-10 is the suppression of HIV replication in monocytes and in related cell lines. The results demonstrate that IL-10 can provide a means of immune defense against HIV by suppressing replication in M/M.

While IL-10 has ability to suppress HIV replication in chronically infected M/M or monocytoid lines, the effects are most pronounced in the setting of acute infection. This suggests that IL-10 has activity at an early stage of HIV replication as well as in the latter stages. The ability of HIV to undergo reverse transcription and form a provirus is dependent on the state of activation of the target cell as well as intracellular nucleoside pools (47, 48). IL-10 can thus influence the rate of proviral formation through its protean effects on M/M activation. However, it should be noted that the suppression of HIV replication is not simply the result of a toxic effect of IL-10 on M/M; as seen in the Examples, the anti-HIV effects occur at concentrations of IL-10 that had little or no effect on cellular viability, protein synthesis, cytokine secretion, phagocytosis, or the ability to present antigen (tetanus toxoid).

Any obstacles to clinical use of IL-10 can be overcome. One potential obstacle is that IL-10's anti-HIV activity is observed predominantly in M/M. This problem, however, can be addressed by administering it with antiretroviral drugs, such as dideoxynucleosides, that have activity in T cells. In this regard, the effects of IL-10 on the activity of these drugs can be screened. Other cytokines that are active in monocyte/macrophages, such as granulocyte-macrophage colony-stimulating factor (GM-CSF), affect the anti-HIV activity of dideoxynucleosides in those cells, in part by modulating their phosphorylation (25, 49), and such interactions can be analyzed for IL-10.

Another potential obstacle to the clinical use of IL-10 in disease caused by HIV is that certain patients with HIV infection may already overproduce IL-10, and its immunosuppressive properties could potentially be deleterious in this setting. One of the hallmark features of HIV infection is overstimulation of B cells in conjunction with a suppression of cellular immunity, and it has been hypothesized that IL-10 overproduction late in the disease may exacerbate this effect. Moreover, Benjamin et. al. have shown that AIDS lymphoma-derived B cell lines often produce IL-10 in vitro, and it has been suggested that this may promote the development of non-Hodgkin's lymphoma, either through stimulation of B cells or through suppression of cellular immunity (34). Finally, as noted above, the ability of IL-10 to block M/M-mediated killing of intra- and extra-cellular parasites may be harmful in patients with HIV-induced immunodeficiency. Even with these concerns, treatment with rhIL-10 can be beneficial in certain patients with HIV infection, particularly in conjunction with other anti-retroviral therapy as discussed above. The anti-HIV effects of IL-10 occur at somewhat lower concentrations than are required to mediate immune functions, and a range of concentrations at which the anti-HIV effects predominate can be determined. Thus, while this cytokine has a number of powerful effects which may be deleterious in the setting of HIV infection, it is possible to exploit its ability to suppress HIV-infection in M/M in a therapeutically beneficial manner. Also, one can engineer a separation of this effect from the other immunological activities of this cytokine by making modifications in IL-10.

The present invention is more particularly described in the following examples which are intended as illustrative only since numerous modifications and variations therein will be apparent to those skilled in the art.

EXAMPLES

Materials and Methods

Cytokines and drugs. The rhIL-10 was obtained from the unpurified or purified supernatants of rhIL-10 cDNA-transfected COS-7 cells as previously described (12). rhIL-10 can also be obtained from PeproTech, Inc., Rocky Hill, N.J. and R&D Systems, Minneapolis, Minn. Supernatants of COS-7 cells transfected with the murine IL-10 gene or mock-transfected cells were used as controls where appropriate. All IL-10 preparations used in the Examples were obtained from Drs. K. W. Moore and P. Viera, DNAX Research Institute, Palo Alto, Calif. One unit of IL-10 is defined as the amount that will produce half-maximal stimulation of the MC/9 mast cell line (6). An MC/9 line is deposited with the American Type Culture Collection under Accession No. CRL-8306. Human recombinant M-CSF (Cellular Products, Buffalo, N.Y.) was used at a concentration of 1000 U/ml Lipopolysaccharide (LPS) from E. coli strain $J_5$ Rc mutant (Sigma, St. Louis, Mo.) was diluted in medium and used at a final concentration of 1 µg/ml. 2'3'-Dideoxyinosine (ddI, Sigma) and sodium azide (Sigma) were diluted in PBS prior to use.

Cell culture. Human mononuclear cells were obtained from the peripheral blood of normal HIV-seronegative donors by use of a cell separator (Fenwal C3000; Baxter-Travenol, Deerfield, Ill.). The cells were then further enriched for M/M by means of countercurrent centrifugal elutriation as previously described (17). The resulting cells were greater than 95% monocytoid when examined after Giemsa staining and were greater than 95% non-specific esterass positive. Cell viability as evaluated by trypan blue exclusion was consistently greater than 95%. More than 93% of the cells were CD11b-and CD36-positive (OKM1 and OKM5, respectively; Ortho Diagnostic Systems, Westwood, Mass.). Other characteristics of these cells have been described elsewhere (18). The cells were cultured in 48- or 96-well plates (Costar, Cambridge, Mass.) in RPMI 1640 medium (Gibco Laboratories, Grand Island, N.Y.) supplemented with 20% heat-inactivated, low endotoxin fetal calf serum (defined FCS; Hyclone Laboratories, Logan, UT), 2 mM 1-glutamine, 50 U/ml penicillin, and 50 µg/ml streptomycin (all from Gibco Laboratories). No proliferation-inducing cytokines, such as M-CSF or GM-CSF, were used in the experiments unless specifically stated. Infection with HIV-1 was performed 4 days after the cells were initially put into culture.

Human mononuclear cells were obtained by Ficoll/sodium diatrizoate (LSM, Organon Teknica, Durham, N.C.) density centrifugation of peripheral blood from normal, HIV-seronegative donors. THP-1 and MOLT-4 cells were obtained from American Type Culture Collection (ATCC, Rockville, Md.). The H9 cell line was obtained from M. Popovic and R. Gallo, Laboratory of Tumor Cell Biology, National Cancer Institute. The cells were all called in 96-well plates in RPMI 1640 medium supplemented with 10% heat-inactivated, low endotoxin fetal calf serum, 2 mM 1-glutamine, 50 U/ml penicillin, and 50 µg/ml streptomycin. ATH-8 cells, a tetanus-toxoid-specific CD4+ T-cell line immortalized by exposure to HTLV-I (19, 20) (provided by H. Mitsuya, National Cancer Institute, Bethesda, Md.) were propagated in the above medium with the addition of 50 U/ml rhIL-2 (R and D Systems, Minneapolis, Minn.) and 20% purified delectinized human IL-2 (ABI, Columbia, Md.). All cell lines were tested and found to be negative for Mycoplasma cantamination.

Viral strains. $HIV-1_{Ba-L}$, a monocytotropic strain of HIV-1 (provided by Drs. S1 Gartner, M. Popovic, and R. Gallo, National Cancer Institute, Bethesda, Md.) was used at a dose of $400 \times TCID_{50}$ for all monocyte/macrophage (M/M) experiments. Infectivity was determined in primary M/M cultures, as previously described (18). $HIV-1_{IIIB}$ (21), a lymphocytotropic strain (Advanced Biotechnologies, Inc., Columbia, Md.) was used for other studies. Doses of $3000 \times TCID_{50}$ in ATH-8 and $1000 \times TCID_{50}$ in H9, MOLT-4, THP-1, and U937 cell lines were employed. The infectivity of $HIV-1_{IIIB}$ was determined using the ATH-8 cell line (20, 22).

Cytokine and virus quantitation. Measurement of IL-1β and TNF-α in culture supernatant was performed by ELISA (R and D Systems) after viral inactivation with Triton-X 100 at a final concentration of 0.5%. Lower limits of detection for IL-1β, and TNF-α were 3.90 pg/ml, and 15.7 pg/ml, respectively. IL-6 was quantitated by bioassay, using the IL-6-dependent lymphocytic cell line B9 after heat inactivation of virus at 55° C. for 30 minutes, as described (23, 24).

Viral production was assessed by HIV-1 p24 antigen (gag) release into culture supernatants as measured by radioimmunoassay (Du Pont Co., Wilmington, Del.); the lower limit of detection was 600 pg/ml. In some experiments, viral production was also assessed by an assay of reverse transcriptase activity (RT-Detect, Du Pont). The cultures were inspected daily by inverted-stage microscopy for syncytia formation and other vitally- and cytokine-induced morphologic effects.

Monocyte viral suppression assay. The assessment of the effects of rhIL-10 on HIV replication in M/M was performed as a modification of a previously published procedure (25). Elutriated M/M were cultured in complete medium at a concentration of $1.25 \times 10^5$ cells/ml in flat-bottomed 96-well culture plates (Costar, Cambridge, Mass.) for 4 days before infection (starting on day -4), and incubated at 37° C. in a humidified 5% $CO_2$ atmosphere. IL-10 was added at either day -2, 0, +5, or +15, and cells were washed extensively to remove the cytokine 48 hours later. On day 0, virus was added to each well (when IL-10 was added at day -2, virus was added just after the cytokine was washed out; when IL-10 was added at day 0, virus was added immediately following addition of the cytokine). On day 2, cells were washed to remove excess virus (and cytokine when added on day 0). Every 5 days, the supernatant was harvested from each well and replaced with fresh complete medium until day +27 was reached. Supernatants were assayed for HIV-1 p24 antigen. Since peak p24 levels are generally noted at day +12 in control wells, we focused on this time point in evaluating the effects of IL-10.

M/M phagocytosis. A modification of the method of Malorny et. al. (26) was used to determine the effect of rhIL-10 on M/M phagocytosis. Elutriated M/M ($2.5 \times 10^5$ cells/1.0 ml well) were cultured in 48-well plates (Costar, Cambridge, Mass.) for 4 days at 37° C. in a humidified 5% $CO_2$ atmosphere, with or without rhIL-10. After 2 days, the wells were washed to remove IL-10, and complete medium was added. Twenty-four hours later, the cells were detached using trypsin, and suspended at $1.5 \times 10^5$ cells/50 µl in medium using 10×75 mm borosilicate glass tubes (Kimble, Vineland, N.J.). 25 µl of a 1:20 dilution of 0.8 µm latex beads (Sigma) in complete medium was added to each tube, vortexed, and incubated at 37° C. for 45 minutes. After incubation, the cell suspension was layered over 1.5 ml FCS and centrifuged at 250×g for 10 minutes at room temperature. Serum and non-phagocytosed beads were removed, and the cells were washed twice with PBS containing 2% BSA and 0.02% sodium azide. Cells found to have ingested three or more beads on microscopic examination were scored as positive for phagocytic activity.

Leucine incorporation assay. Incorporation of [$^3$H]-leucine in monocytes was measured using a modification of the procedure of Bonifacino (27). Monocytes were cultured on 48-well plates ($2.5\times10^5$ cells/1.0 ml well) for 4 days at 37° C. in a humidified 5% $CO_2$ atmosphere. The cells were washed, medium containing purified rhIL-10 or control medium was added, and plates were incubated for 48 hours at 37° C. in a 5% $CO_2$ atmosphere. The cells were again washed, M-CSF 1000 U/ml or sodium azide 0.02% was added to certain wells as a positive and negative control for protein synthesis, and the cells were incubated for 12 hours. The cells were washed with leucine-free medium (RPMI 1640 without leucine, Gibco) supplemented with 20% dialyzed fetal bovine serum and 2 mM 1-glutamine (Gibco) and incubated for 3 hours in this medium with 0.2 mCi/ml [$^3$H]-leucine (Amersham, Arlington Heights, Ill.). After incubation, proteins were precipitated with 1:1 ice-cold 10% trichloroacetic acid, followed by 30 minutes incubation at 4° C. Precipitated proteins were collected on glass fiber filters, and washed three times with cold 10% TCA, then twice with absolute ethanol. The filters were dried and counted in scintillation cocktail. At least three replicate wells were established for each data point.

Human peripheral blood mononuclear cell proliferative responses. Freshly isolated human peripheral blood mononuclear cells were washed and cultured at a density of $1\times10^6$/ml in 200 µl wells in 96-well round-bottom plates with various concentrations of rhIL-10. Where indicated, PHA (Sigma) 0.5 or 5.0 µg/ml, tetanus toxoid (Commonwealth of Massachusetts Department of Public Health, Jamaica Plain, N.Y.) 1.0 LF/ml, or mouse anti-human CD3 monoclonal OKT3 antibody (a gift of Ortho Pharmaceutical Corp., Raritan, N.J.) 20 ng/ml were added as stimulators. A relatively low concentration of PHA (0.5 µg/ml) was used along with the higher dose of 5.0 µg/ml, as the suppression of PHA-induced proliferation by rhIL-10 has been shown to be more evident with lower doses of mitogen (28). Triplicate wells were established for each condition examined. Plates were incubated for 3 days for PHA stimulation and 5 days for the other proliferative stimuli at 37° C. in a humidified 5% $CO_2$ atmosphere, and pulsed with 1.0 µCi [$^3$H]-thymidine during the final 18 hours of incubation. The cultures were then harvested onto glass fiber filters and counted in liquid scintillation cocktail.

Assay of HIV replication in cell lines. Uninfected or chronically $HIV_{IIIB}$-infected cell lines in exponential growth phase were washed and cultured at a density of $5.0\times10^3$ cells/ml in 200 µl wells in 96-well flat-bottom culture plates (Costar). COS-7 supernatant containing rhIL-10 or rhIL-10 at 20 U/ml, mock-transfected COS-7 supernatant, or control medium was added as indicated, followed within 30 minutes by an inoculum of HIV-1 ($1000\times TCID_{50}$). The plates were incubated for 5 days at 37° C. in a humidified 5% $CO_2$ atmosphere. Supernatants were then harvested for p24 antigen determination, and the cells were counted by hemocytometer using trypan blue. "Percent suppression" is expressed as $[1-(p24\ Ag_{IL-treated}/p24\ Ag_{control})]\times 100\%$.

Inhibition assay for the cytopathic effect of HIV-1. The assay was performed as a modification of Mitsuya et. al. (20). ATH-8 cells were cultured at a density of $2.5\times10^5$ cells/ml in 96-well U-bottom plates with human or murine IL-10 at a concentration of 20 U/ml, ddI 20 µM (Sigma), or control medium. After 30 minutes, the cells were inoculated with HIV ($3000\times TCID_{50}$), and incubated at 37° C. in a 5% $CO_2$ atmosphere for 7 days. Viable cells were counted using trypan blue exclusion, and the data were expressed as the percentage of viable cells as compared with uninfected, untreated controls.

Results rhIL-10 inhibits HIV replication in M/M. In initial experiments designed to evaluate the effects of rhIL-10 on HIV replication, M/M obtained by elutriation were pre-cultured in complete medium for 4 days and then simultaneously exposed to purified rhIL-10 and 400 $TCID_{50}$ $HIV_{Ba-L}$ (day 0). After 2 days, the cells were washed extensively and cultured for another 12 days without additional cytokine or virus. Four-day-precultured elutriated human M/M were exposed to varying doses of purified rhIL-10, and immediately inoculated with $HIV-1_{Ba-L}$ ($400\times TCID_{50}$). After 2 days, the cells were washed and cultured without further addition of IL-10 or HIV. The medium was again replaced at day 7 and 12. The rhIL-10 (present from day 0 to 2) strongly inhibited p24 production at day 12 in a dose-dependent manner. A similar effect was seen when reverse transcriptase in the supernatants were assayed as an alternate measure of viral replication. Suppression of p24 production was seen at relatively low concentrations of rhIL-10; the $ID_{50}$ under these conditions was approximately 0.03 U/ml. In control experiments, recombinant murine IL-10 (rmIL-10 as a COS-7 supernatant) was approximately 30 times less active than rhIL-10.

The time course of p24 production in cultures exposed to rhIL-10 on days 0 to 2 was examined as follows. Elutriated human M/M, precultured for four days, were cultured with purified rhIL-10 and immediately exposed to $HIV-1_{Ba-L}$ at a dose of $400\times TCID_{50}$. After 2 days, the cells were washed with fresh medium, and incubation was continued. Supernatants were harvested every 5 days thereafter, and replaced with fresh medium. A 2-day exposure of M/M to 0.1 to 1 U/ml of rhIL-10 resulted in a 7 to 10 day delay in the production of HIV. However, rhIL-10 did not completely abrogate HIV replication in M/M.

Effects of late addition of rhIL-10 to M/M. In subsequent experiments, we explored the effects of rhIL-10 added to cultures of M/M previously exposed to HIV. Four-day-precultured elutriated human M/M were infected with $HIV-1_{Ba-L}$ at a dose of $400\times TCID_{50}$, and washed with fresh medium after 2 days. HIV p24 antigen levels in the supernatants were measured. Purified rhIL-10 1U/ml, rhIL-10 0.1 U/ml, or control medium were added to the cultures starting either at day 5 after infection (A) or at day 15 (B) after infection and washed out after 2 days. Supernatants were harvested every 5 days and replaced with fresh medium. The rhIL-10 suppressed HIV production in M/M cultures even when added for two days starting on day 5 or day 15. At these timepoints, productive infection of the cultures was already established, and the results demonstrate that rhIL-10 can suppress HIV production in M/M already infected by HIV. However, this late suppression could result from rhIL-10 interfering with the spread of infection in these cultures.

In additional experiments, we explored the effects of rhIL-10 added to M/M during the 2 days prior to the addition of HIV, and then washed out at the time of viral exposure. Elutriated human M/M were precultured for 4 days in medium alone and then exposed to $HIV_{Ba-L}$ at a dose of $400\times TCID_{50}$. Various dilutions of rhIL-10 were added to the plates for 2 days, starting either 2 days prior to the addition of HIV (day −2 to day 0; stippled bars) or at the time of HIV addition (day 0 to day 2; black bars). The cells were washed immediately before, 2 days after, and 7 days after HIV infection. Supernatants were harvested on day 12 and assayed for HIV p24 antigen. Only modest (37%) suppression was observed when cells were exposed to 1 U/ml of rhIL-10 between days −2 and 0, as compared to the nearly complete (91%) suppression observed when cells were exposed to the same amount of rhIL-10 between day 0 and 2. Thus, rhIL-10 has relatively little effect on HIV infection of M/M if washed out at the time virus is added.

Effects of rhIL-10 on the viability and function of mononuclear cells. We next asked whether these effects resulted from a toxic effect of rhIL-10 on M/M. As seen in Table 1, a two-day exposure of M/M to rhIL-10 at concentrations of up to 1 U/ml had essentially no effect on the number of viable cells when examined by Trypan blue exclusion at either day 2 or day 7. Moreover, concentrations of rhIL-10 up to 1 U/ml had no effect on the ability of M/M to phagocytosed latex beads on day 3. We also examined the effect of rhIL-10 on [$^3$H]-leucine incorporation into M/M, a measure of protein synthesis. Slight inhibition was observed at 1 U/ml of rhIL-10, while no effect was observed at lower concentrations. Thus, HIV replication in M/M was suppressed by rhIL-10 at concentrations that had little or no effect on the number of viable cells, their phagocytic activity, or their protein synthesis.

It has been reported (5) that secretion of various cytokines (including IL-1β, IL-6, and TNF-α) by endotoxin-stimulated M/M is inhibited by relatively high concentrations of human IL-10 (100 U/ml). We were interested to learn whether the lower concentrations of rhIL-10 found here to inhibit HIV replication in M/M also inhibited production of these cytokines. M/M were incubated either in medium alone or with purified rhIL-10 for 48 hours, washed, and immediately treated with LPS for 12 hours. Supernatants were then harvested and assayed for IL-1β, IL-6, and TNF-α. As shown in Table 2, IL-6 production was marginally decreased by rhIL-10 at the highest concentration used (1.0 U/ml), while IL-1β and TNF-α production were not affected. In additional experiments, we found no effect on the LPS-induced production of IL-6 5 days after a 2-day pulse of rhIL-10 at concentrations up to 10 U/ml (data not shown). Therefore, rhIL-10 inhibited HIV replication in M/M at concentrations that had little or no effect on endotoxin-induced cytokine production.

As another measure of the immunosuppressive actions of rhIL-10 at these lower concentrations, we evaluated the effects of rhIL-10 on mononuclear cell proliferation induced by tetanus toxoid, phytohemagglutinin, and OKT3 monoclonal antibody (anti-CD3). Unlike the experiments with HIV in M/M, in which viral suppression was seen with a 2 day exposure to rhIL-10, the mononuclear cells were continuously exposed to rhIL-10 throughout the incubation period. Even so, there was no significant inhibition of cellular proliferation as measured by [$^3$H]-thymidine incorporation, until a rhIL-10 concentration of 1–10 U/ml was attained. These data show that the effects of IL-10 on HIV replication in monocytes may occur at a different range of concentrations than those that cause a downregulation of cellular immune functions.

Effect of rhIL-10 on HIV replication in T cell and monocytoid cell lines. To further characterize the range of cell types in which rhIL-10 had anti-HIV activity, we examined its ability to suppress HIV replication in the CD4+ T cell lines H9 and MOLT-4 as well as in the monocytoid lines THP-1 and U937. As seen in Table 4, a 5-day continuous exposure to 20 U/ml rhIL-10, starting at the time of infection with HIV$_{IIIB}$, had no effect on HIV p24 production by MOLT-4 or H9 CD4+ T cells. This concentration of rhIL-10 also failed to inhibit HIV replication by acutely infected THP-1 monocytoid cells. By contrast, 20 U/ml rhIL-10 inhibited HIV production by acutely infected U937 promonocytic cells by 63%. Moreover, HIV production by U937 cells chronically infected with HIV was suppressed by 30% following exposure to 20 U/ml IL-10. These effects occurred in spite of the fact that rhIL-10 at these concentrations had no effect on the proliferation of those cell lines. Thus, rhIL-10 can partially inhibit HIV replication in U937 cells at the relatively high concentration of 20 U/ml.

We next assessed the activity of rhIL-10 in ATH-8, an HTLV-1-immortalized tetanus-toxoid-specific CD4+ T-cell line that is profoundly sensitive to the cytopathic effect of HIV-1 (19, 20). In the absence of rhIL-10, HIV$_{IIIB}$ infection reduced the number of viable ATH8 cells to 8% of control over 7 days of culture (Table 5). In the presence of 20 U/ml of rhIL-10, some protection from HIV-induced cytopathicity was observed (viable cells 39% of uninfected control). This concentration of rhIL-10 caused no inhibition of cell proliferation in the absence of HIV infection (113% of control), demonstrating that the anti-HIV effect was not simply due to cellular toxicity. In contrast to human IL-10, murine recombinant IL-10 (rmIL-10) had little or no effect on HIV-induced cytopathicity in this system. While it should be stressed that the protection afforded by rhIL-10 in this T cell line is substantially less than that induced by ddI, a dideoxynucleoside anti-HIV agent (100% suppression at a concentration of 20 μM), the results still demonstrate a modest protective effect.

Throughout this application, various publications are referenced. The disclosures of these publications in their entireties are hereby incorporated by reference into this application in order to more fully describe the state of the art to which this invention pertains.

TABLE 1

Effects of rhIL-10 on M/M Viability and Function

| hIL-10 (U/ml) | # Viable Cells (% Control) | | Phagocytic Cells (% Control) | 3H-Leucine Incorporation (% Control) |
|---|---|---|---|---|
| | Day 2 | Day 7 | Day 3 | Day 3 |
| 0 | 100 | 100 | 100 | 100 |
| 1 | 105.7 | 118.2 | 112.4 | 63.1 |
| 0.1 | ND | ND | 99.7 | 108.4 |
| 0.01 | ND | ND | 101.9 | 114.9 |

Four-day-preincubated M/M at a concentration of $1.25 \times 10^5$ cells/ml were exposed to rhIL-10 (0.01–1.0 U/ml) for two days (days 0–2). The cells were then harvested for determination of viability on day 2, or cultured for 5 additional days in fresh medium and then harvested. For phagocytosis of latex beads or incorporation of $^3$H-leucine, the cells were cultured for 24 hours after the exposure to rhIL-10. Absolute values of controls are as follows: Number of viable cells, $4.7 \times 10^4$ cells/ml on day 2 and $9.5 \times 10^3$ cells/ml on day 5; phagocytically active cells, 79.1%; $^3$H-leucine incorporation, 44300 cpm. ND = not done.

TABLE 2

LPS-Induced Cytokine Secretion in rhIL-10-Treated M/M

| IL-10 (U/ml) | LPS Stimulation | IL-1-beta (pg/ml) | TNF-alpha (pg/ml) | IL-6 (U/ml) |
|---|---|---|---|---|
| — | — | <3.90 | 68.48 (52.78) | <2 |
| — | + | 36.53 (5.52) | 1155.18 (201.55) | 39.90 (10.21) |
| 1 | + | 39.62 (2.36) | 941.56 (365.01) | 23.87 (2.98) |
| 0.1 | + | 33.99 (2.10) | 505.03 (61.68) | 26.63 (4.45) |
| 0.01 | + | 20.59 (1.22) | 1024.77 (218.03) | 53.27 (13.48) |

Four-day-preincubated M/M were incubated with various concentrations of rhIL-10 or control medium for 2 days (days 0–2), and then washed. At that time, LPS (1 μg/ml) was added. Twelve hours later, supernatants were harvested for determination of cytokine levels. Results shown are mean (SEM) of triplicate determinations.

TABLE 3

Effect of IL-10 on Mononuclear Cell Proliferative Responses

| | Stimulus | | | |
|---|---|---|---|---|
| | PHA 0.5 μg/ml | PHA 5.0 μg/ml | Tetanus toxoid | OKT3 |
| Unstimulated | 749 (73.0) | 512 (39.1) | 1965 (736.5) | 1541 (241.6) |
| Medium alone | 41389 (1148.2) | 87000 (1522.0) | 5552 (1135.6) | 12313 (486.2) |
| rhIL-10 0.01 U/ml | 43571 (933.1) | 83466 (2870.6) | 5348 (397.3) | 15970 (2266.5) |
| rhIL-10 0.1 U/ml | 42101 (2784.6) | 84559 (1697.8) | 4219 (398.7) | 15159 (2408.5) |
| rhIL-10 1.0 U/ml | 41047 (3452.9) | 77941 (4917.1) | 6630 (1402.1) | 10743 (2532.9) |
| rhIL-10 10 U/ml | 19461 (234.6) | 88246 (1854.2) | 1817 (947.1) | 2386 (429.7) |
| rhIL-10 100 U/ml | 15596 (1583.6) | 80794 (2209.5) | 895 (1072.8) | 2268 (894.7) |

Freshly isloated normal human peripheral blood mononuclear cells were cultured at a density of $1 \times 10^6$/ml in 200 μl wells in 96-well flat bottom plates with various concentrations of rhIL-10. PHA 0.5 or 5.0 μg/ml, tetanus toxoid 1.0 LF/ml, or OKT3 antibody 20 ng/ml were added as stimulators. Plates were incubated for 3 days for PHA stimulation and 5 days for the other proliferative stimuli. They were then pulsed with 1.0 μCi/well $^3$H-thymidine 18 hours before completion of the incubation period. The cultures were then harvested onto glass fiber filters and counted. Results are expressed as mean cpm/well (SEM) of sextuplicate observations.

TABLE 4

Effect of IL-10 on HIV Replication in Acutely and Chronically Infected Cell Lines

| | | % Suppression p24 Ag | |
|---|---|---|---|
| Cell Line | Cell Type | hIL-10 (20 U/ml) | mIL-10 (20 U/ml) |
| H-9 Acutely Infected | CD4 + T | 0.0 | 3.0 |
| H9-Chronically Infected | CD4 + T | 0.0 | 0.0 |
| MOLT-4 Acutely Infected | CD4 + T | 8.6 | 8.6 |
| U937-Acutely Infected | Promonocytic | 63.5 | 15.6 |
| U937-Chronically Infected | Promonocytic | 32.2 | 5.0 |
| THP-1 Acutely Infected | Monocytic | 23.3 | 0.0 |

Cells from the indicated cell lines at a density of $1.0 \times 10^3$ per 200 μl well were cultured in either rhIL-10, rmIL-10, or control medium and incubated for 5 days. Acutely infected cell lines were exposed to $HIV_{IIIB}$ at a does of 3000 X $TCID_{50}$ at the beginning of the culture period. Supernatants were harvested and assayed for HIV p24 antigen. The number of viable cells was determined for each line by trypan blue exclusion; in no case did the exposure to rhIL-10 or rmIL-10 induce a >10% change in the number of viable cells.

TABLE 5

Reduction of HIV-Induced Cytopathic Effect by rhIL-10

| | Number of Viable Cells (% Control) | |
|---|---|---|
| | No HIV | HIV |
| No treatment | 100.0 | 8.1 |
| hIL-10 20 U/ML | 112.9 | 39.6 |
| mIL-10 20 U/ML | 123.9 | 10.2 |
| ddI 20 μM | ND | 91.0 |

TABLE 5-continued

Reduction of HIV-Induced Cytopathic Effect by rhIL-10

| | Number of Viable Cells (% Control) | |
|---|---|---|
| | No HIV | HIV |

ATH-8 cells ($5 \times 10^4$ per 200 μl well) were cultured in medium alone, or with rhIL-10, rmIL-10, or ddI, and exposed to $HIV_{IIIB}$ at a dose of $3000 \times TCID_{50}$. The cells were cultured for 7 days, at which time the number of viable cells was determined by trypan blue exclusion. The results here, the average of 2 experiments, are presented as the percentage of viable cells compared with the uninfected, untreated controls (average 87900 viable cells/well at day 7). ND = not done.

References

1. Fiorentino, D. F., M. W. Bond, and T. R. Mosmann. 1989. Two types of mouse T helper cell. IV. Th2 clones secrete a factor that inhibits cytokine production by Th1 clones. *J Exp Med.* 170:2081.
2. Howard, M., A. O'Garra, H. Ishida, R. De Waal Malefyt, and J. De Vries. 1992. Biological properties of interleukin-10. *J Clin Immunol.* 12:239.
3. Go, N. F., B. E. Castle, R. Barrett, R. Kastelein, W. Dang, T. R. Mosmann, K. W. Moore, and M. Howard. 1990. Interleukin 10, a novel B cell stimulatory factor: unresponsiveness of X chromosome-linked immunodeficiency B cells. *J Exp Med.* 172:1625.
4. Bogdan, C., Y. Vodovotz, and C. Nathan. 1991. Macrophage deactivation by interleukin 10. *J Exp Med.* 174:1549.
5. de Waal Malefyt, R., J. Abrams, B. Bennett, C. G. Figdor, and J. E. de Vries. 1991. Interleukin 10(IL-10) inhibits cytokine synthesis by human monocytes: an autoregulatory role of IL-10 produced by monocytes. *J Exp Med.* 174:1209.
6. Thompson-Snipes, L., V. Dhar, M. W. Bond, T. R. Mosmann, K. W. Moore, and D. M. Rennick. 1991. Interleukin 10: a novel stimulatory factor for mast cells and their progenitors. *J Exp Med.* 173:507.
7. MacNeil, I. A., T. Suda, K. W. Moore, T. R. Mosmann, and A. Zlotnik. 1990. IL-10, a novel growth cofactor for mature and immature T cells. *J Immunol.* 145:4167.
8. Vieira, P., R. de Waal Malefyt, M. N. Dang, K. E. Johnson, R. Kastelein, D. F. Fiorentino, J. E. deVries, M. G. Roncarolo, T. R. Mosmann, and K. W. Moore. 1991. Isolation and expression of human cytokine synthesis inhibitory factor cDNA clones: homology to Epstein-Barr virus open reading frame BCRFI. *Proc Natl Acad Sci U S A.* 88:1172.
9. O'Garra, A., G. Stapleton, V. Dhar, M. Pearce, J. Schumacher, H. Rugo, D. Barbis, A. Stall, J. Cupp, K. Moore, P. Viera, T. Mosmann, A. Whitmore, L. Arnold, G. Haughton, and M. Howard. 1990. Production of cytokines by mouse B cells: B lymphomas and normal B cells produce interleukin 10. *Int Immunol.* 2:821.
10. O'Garra, A., R. Chang, N. Go, R. Hastings, G. Haughton, and M. Howard. 1992. Ly-1 B (B-1) cells are the main source of B cell-derived interleukin 10. *Eur J Immunol.* 22:711.
11. Fiorentino, D. F., A. Zlotnik, T. R. Mosmann, M. Howard, and A. O'Garra. 1991. IL-10 inhibits cytokine production by activated macrophages. *J Immunol.* 147:3815.
12. Hsu, D. H., R. de WaalMalefyt, D. F. Fiorentino, M. N. Dang, P. Vieira, J. de Vries, H. Spits, T. R. Mosmann, and K. W. Moore. 1990. Expression of interleukin-10 activity by Epstein-Barr virus protein BCRF1. *Science.* 250:830.
13. Thorley-Lawson, D. A. 1980. The suppression of Epstein-Parr virus infection in vitro occurs after infection but before transformation of the cell. *J Immunol.* 124:745.

14. Masucci, M. G., M. T. BeJarano, G. Masucci, and E. Klein. 1983. Large granular lymphocytes inhibit the in vitro growth of autologous Epstein-Parr virus-infected B cells. *Cell Immunol.* 76:311.

15. Gazzinelli, R. T., M. Makino, S. K. Chattopadhyay, C. M. Snapper, A. Sher, A. W. Hugin, and H. C. Morse III. 1992. CD4+ subset regulation in viral infection. Preferential activation of Th2 cells during progression of retrovirus-induced immunodeficiency in mice. *J Immunol.* 148:182.

16. Clerici, M., F. T. Hakim, D. J. Venson, S. Blatt, C. W. Hendrix, T. A. Wynn, and G. M. Shearer. 1992. Changes in interleukin 2 and interleukin 4 production in asymptomatic, HIV-seropositive individuals. *J Clin Invest.* In press.

17. Gerrard, T. L., C. H. Jurgensen, and A. S. Fauci. 1983. Differential effect of monoclonal anti-DR antibody on monocytes in antigen- or mitogen-stimulated response: mechanism of inhibition and relationship to interleukin-1 secretion. *Cell. Immunol.* 82:394.

18. Perno, C.-F., M. W. Baseler, S. Proder, and R. Yarchoan. 1990. Infection of monocytes by human immunodeficiency virus i is blocked by inhibitors of CD4-gp120 binding, even in the presence of enhancing antibodies. *J Exp Med.* 171:1043.

19. Mitsuya, H., K. J. Weinhold, P. A. Furman, M. H. St. Clair, S. Nusinoff Lehrman, R. C. Gallo, D. Bolognesi, D. W. Barry, and S. Proder. 1985. 3'-Azido-3'-deoxythymidine (BW A509U): an antiviral agent that inhibits the infectivity and cytopathic effect of human T-lymphotropic virus type III/lymphadenopathy-associated virus in vitro. *Proc. Natl. Acad. Sci. USA.* 82:7096.

20. Mitsuya, H., M. Matsukura, and S. Broder. 1987. Rapid in vitro systems for assessing activity of agents against HTLV-III/LAV. S. Broder, eds. AIDS: modern concepts and therapeutic challenges. Marcel Dekker, New York. 303.

21. Wain-Hobson, H. S., J.-P. Vartanian, M. Henry, N. Chenciner, R. Cheynier, S. Delassus, L. P. Martins, M. Sala, M.-T. Nugeyre, D. Guetard, D. Klatzmann, J.- C. Gluckman, W. Rozenbaum, F. Barre-Sinoussi, and L. Montagnier. 1991. LAV revisited: origins of the early HIV-1 isolates from Institut Pasteur. *Science.* 252:961.

22. Leland, D. S., and M. L. V. French. 1988. Virus isolation and identification. E. H. Lennette, P. Halonen and F. A. Murphy, eds. Laboratory diagnosis of infectious diseases. Springer-Verlag, New York. 49.

23. Aarden, L. A., E. R. De Groot, O. L. Schaap, and P. M. Lansdorp. 1987. Production of hybridoma growth factor by human monocytes. *Eur. J. Immunol.* 17:1411.

24. Nordan, R. P. 1991. Measurement of mouse and human interleukin 6. J. E. Coligan, A.M. Kruisbeek, D. H. Margulies, E. M. Shevach and W. Strober, eds. Current protocols in immunology. John Wiley and Sons, New York. Section 6.

25. Perno, C.-F., R. Yarchoan, D. A. Cooney, N. R. Hartman, D. S. A. Webb, Z. Hao, H. Mitsuya, D. G. Johns, and S. Broder. 1989. Replication of human immunodeficiency virus in monocytes. Uranulocyte/macrophage colony-stimulating factor (GM-CSF) potentiates viral production yet enhances the antiviral effect mediated by 3'-azido-2'3'-dideoxythymidine (AZT) and other dideoxynucleoside congeners of thymidine. *J. Exp. Med.* 169:933.

26. Malorny, U., C. Neumann, and C. Sorg. 1981. Influence of various detachment procedures on the functional state of cultured murine macrophages. *Immunobiol.* 159:327.

27. Bonifacino, J. S. 1991. Biosynthetic labeling of proteins. J. E. Coligan, A. M. Kruisbeek, D. H. Margulies, E. M. Shevach and W. Strober, eds. Current Protocols in Immunology. John Wiley and Sons, New York. Section 8.

28. Taga, K., and G. Tosato. 1992. IL-10 inhibits human T cell proliferation and IL-2 production. *J Immunoi.* 148:1143.

29. Zlotnik, A., and K. W. Moore. 1991. Interleukin 10. *Cytokine.* 3:366.

30. Gazzinelli, R. T., I. P. Oswald, S. L. James, and A. Sher. 1992. IL-10 inhibits parasite killing and nitrogen oxide production by IFN-gamma-activated macrophages. *J Immunol.* 148:1792.

31. Oswald, I. P., R. Taazzinelli, A. Sher, and S. L. James. 1992. IL-10 synergizes with IL-4 and transforming growth factor-beta to inhibit macrophage cytotoxic activity. *J Immunoi.* 148:3578.

32. Oswald, I. P., T. A. Wynn, A. Sher, and S. L. James. 1992. Interleukin 10 inhibits macrophage microbicidal activity by blocking the endogenous production of tumor necrosis factor $\alpha$ required as a costimulatory factor for interferon $\gamma$-induced activation. *J Immunol.* 89:8676.

33. Sher, A., D. Fiorentino, P. Caspar, E. Pearce, and T. Mosmann. 1991. Production of IL-10 by CD4+ T lymphocytes correlates with down-regulation of Th1 cytokine synthesis in helminth infection. *J Immunol.* 147:2713.

34. Benjamin, D., T. J. Knobloch, and M. A. Dayton. 1992. Human B-cell interleukin-10: B-cell lines derived from patients with acquired immunodeficiency syndrome and Burkitt's lymphoma constitutively secrete large quantities of interleukin-10. *Blood.* 80:1289.

35. Burdin, N., C. Péronne, J. Banchereau, and F. Rousset. 1993. Epstein-Bart virus transformation induces B lymphocytes to produce human interleukin 10. *J Exp Med.* 177:295.

36. Defrance, T., B. Vanbervliet, F. Briere, I. Durand, F. Rousset, and J. Banchereau. 1992. Interleukin 10 and transforming growth factor beta cooperate to induce anti-CD40-activated naive human B cells to secrete immunoglobulin A. *J Exp Med.* 175:671.

37. Rousset, F., E. Garcia, T. Defrance, C. Peronne, N. Vezzio, D. H. Hsu, R. Kastelein, K. W. Moore, and J. Banchereau. 1992. IL-10 is a potent growth and differentiation factor for activated human B lymphocytes. *Proc Natl Acad Sci.* 89:1890.

38. Stewart, J. P., and C. M. Rooney. 1992. The interleukin-10 homolog encoded by Epstein-Barr virus enhances the reactivation of virus-specific cytotoxic T cell and HLA-unrestricted killer cell responses. *Virology.* 191:773.

39. Gartner, S., P. Markovits, D. M. Markovitz, M. H. Kaplan, and R. C. Gallo. 1986. The role of mononuclear phagocytes in HTLV-III/LAV infection. *Science.* 233:215.

40. Fauci, A. S. 1988. The human immunodeficiency virus: infectivity and mechanisms of pathogenesis. *Science.* 239:617.

41. Zon, L. i., C. Arkin, and J. E. Groopman. 1987. Haematologic manifestations of the human immunodeficiency virus (HIV). *British J. Haem.* 66:251.

42. Gendelman, H. F., J. M. Orenstein, M. A. Martin, C. Ferrua, R. Mitra, T. Phipps, L. Wahl, H. C. Lane, A. S. Fauci, D. S. Burke, D. Skillman, and M. S. Meltzer. 1988. Efficient isolation and propagation of human immunodeficiency virus on recombinant colony-stimulating factor 1-treated monocytes. *J. Exp. Med.* 167:1428.

43. Koenig, S., H. E. Gendelman, J. M. Orenstein, M. C. Dal Canto, G. H. Pezeshkpour, M. Yungbluth, F. Janotta, A. Aksamit, M. Martin, and A. S. Fauci. 1986. Detection of AIDS virus in macrophages in brain tissue from AIDS patients with encephalopathy. *Science.* 233:1089.
44. Liebermann, T. A., and D. Baltimore. 1990. Activation of the interleukin-6 gene through the NF-κB transcription factor. *Mol Cell Biol.* 10:2327.
45. Nable, G. J., and D. Baltimore. 1987. An inducible transcriptional factor activates expression of human immunodeficiency virus in T cells. *Nature.* 326:711.
46. Poli, G., P. Bressler, A. Kinter, E. Duh, W. C. Timmer, A. Rabson, J. S. Justement, S. Stanley, and A. S. Fauci. 1990. Interleukin 6 induces human immunodeficiency virus expression in infected monocytic cells alone and in synergy with tumor necrosis factor alpha by transcriptional and post-transcriptional mechanisms. *J. Exp. Med.* 172:151.
47. Zack, J. A., A.M. Halslip, P. Krogstad, and I. S. Chen. 1992. Incompletely reverse-transcribed human immunodeficiency virus type 1 genomes in quiescent cells can function as intermediates in the retroviral life cycle. *J Virol.* 66:1717.
48. Zack, J. A., S. J. Arrigo, S. R. Weltsman, A. S. Go, A. Haislip, and I. S. Chen. 1990. HIV-1 entry into quiescent primary lymphocytes: molecular analysis reveals a labile, latent viral structure. *Cell.* 61:213
49. Perno, C. F., D. A. Cooney, W. Y. Gao, Z. Hao, D. G. Johns, A. Foli, N. R. Hartman, R. Calio, S. Broder, and R. Yarchoan. 1992. Effects of bone marrow stimulatory cytokines on human immunodeficiency virus replication and the antiviral activity of dideoxynucleosides in cultures of monocyte/macrophages. *Blood.* 80:995.
50. Singer, A., and G. M. Shearer. 1986. AIDS therapy by blocking CD4+ cells (letter). *Nature.* 320:113.
51. Tosato, G., J. Tanner, K. D. Jones, M. Revel, and S. Pike. 1990. Identification of interleukin-6 as an autocrine growth factor for Epstein-Bart virus-immortalized B cells. *J Virol.* 64:3033.
52. Tanner, J., and G. Tosato. 1991. Impairment of natural killer functions by interleukin 6 increases lymphoblastoid cell tumorigenicity in athymic mice. *J Clin Invest.* 88:239.
53. Scala, G., I. Quinto, M. R. Rococo, A. Arcucci, M. Mallardo, P. Caretto, G. Forni, and S. Venuta. 1990. Expression of an exogenous interleukin 6 gene in human Epstein Barr virus B cells confers growth advantage and in vivo tumorigenicity. *J. Exp. Med.* 172:61.
54. Chen, W. F., and A. Zlotnik. 1991. IL-10: a novel cytotoxic T cell differentiation factor. *J Immunol.* 147:528.
55. Sambrook et al., *Molecular Cloning: A Laboratory Manual,* 2nd Ed., Cold Spring Harbor Laboratory, Cold Spring Harbor, N.Y. (1989)
56. Martin, E. W. (ed.) *Remington's Pharmaceutical Sciences,* latest edition Mack Publishing Co., Easton, Pa.

What is claimed is:

1. A method of therapeutically inhibiting the replication of human immunodeficiency virus in human cells in or from a human subject comprising administering to the cells a replication inhibiting amount of interleukin-10.

2. The method of claim 1, wherein the cells are in a human subject and the interleukin-10 administration is parenteral.

3. The method of claim 1, wherein the cells are in a human subject and the interleukin-10 administration is sublingual.

4. The method of claim 1, wherein the interleukin-10 is administered to blood cells removed from a subject and returned after treatment.

5. The method of claim 4, wherein the amount of interleukin-10 administered is between about 0.001 and 1 units/ml.

6. The method of claim 4, wherein the amount of interleukin-10 administered is between about 0.01 and 1 units/ml.

7. The method of claim 1, further comprising administering a compound having anti-human immunodeficiency virus activity.

8. The method of claim 7, wherein the compound is selected from the group consisting of zidovudine, zalcitabine, didanosine and stavudine.

9. The method of claim 1, wherein the cells are selected from the group consisting of monocytes, macrophages and monocyte derived cells.

10. A method of treating a disease caused by human immunodeficiency virus in a human subject comprising administering a replication inhibiting amount of interleukin-10 to the subject.

11. The method of claim 10, wherein the interleukin-10 administration is parenteral.

12. The method of claim 10, wherein the administration is sublingual.

13. The method of claim 10, wherein the interleukin-10 is administered to blood removed from the subject and returned after treatment.

14. The method of claim 10, wherein the amount of interleukin-10 administered is between about 1,000 and 1,000,000 units.

15. The method of claim 10, wherein the amount of interleukin-10 administered is between about 20,000 and 200,000 units.

16. The method of claim 10, further comprising administering a compound having anti-human immunodeficiency virus activity.

17. The method of claim 16, wherein the compound is selected from the group consisting of zidovudine, zalcitabine, didanosine and stavudine.

18. The method of claim 10, wherein the disease is acquired immunodeficiency syndrome.

19. The method of claim 10, wherein the disease is human immunodeficiency virus disease.

20. The method of claim 10, wherein the disease is human immunodeficiency virus associated dementia.

21. The method of claim 10, wherein the disease is autoimmune disease.

22. A method of inhibiting retroviral replication in a human subject infected by a retrovirus comprising administering to the subject an inhibiting amount of interleukin-10.

23. The method of claim 22, wherein the interleukin-10 administration is parenteral.

24. The method of claim 22, wherein the interleukin-10 administration is sublingual.

25. The method of claim 22, wherein the amount of interleukin-10 administered is between about 1,000 and 1,000,000 units.

26. The method of claim 22, wherein the mount of interleukin-10 administered is between about 20,000 and 200,000 units.

27. The method of claim 22, wherein the interleukin-10 is administered to blood removed from the subject and returned after treatment.

28. The method of claim 22, further comprising administering a compound having anti-retrovirus activity.

29. The method of claim 28, wherein the compound is selected from the group consisting of zidovudine, zalcitabine, didanosine and stavudine.

30. A method of treating Kaposi's sarcoma in a human subject comprising administering to the subject an effective amount of interleukin-10 to the subject.

* * * * *